United States Patent
Graumann et al.

(10) Patent No.: US 6,382,835 B2
(45) Date of Patent: May 7, 2002

(54) MOBILE X-RAY APPARATUS AND METHOD FOR DETERMINING PROJECTION GEOMETRIES THEREIN

(75) Inventors: Rainer Graumann, Hoechstadt; Jochen Kusch, Effeltrich, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/771,774

(22) Filed: Jan. 29, 2001

(30) Foreign Application Priority Data

Jan. 27, 2000 (DE) .......................................... 100 03 524

(51) Int. Cl.[7] ................................................. H05G 1/02
(52) U.S. Cl. ........................ 378/198; 378/196; 378/197
(58) Field of Search ................................. 378/196, 197, 378/198

(56) References Cited

U.S. PATENT DOCUMENTS

| | | | |
|---|---|---|---|
| 4,411,012 A | * 10/1983 | Pfeiler et al. | .................. 378/17 |
| 5,583,909 A | 12/1996 | Hanover | |
| 5,822,396 A | 10/1998 | Navab et al. | |
| 5,835,563 A | 11/1998 | Navab et al. | |
| 5,852,646 A | 12/1998 | Klotz et al. | |
| 6,120,180 A | 9/2000 | Graumann | |
| 6,131,690 A | * 10/2000 | Galando et al. | ............. 180/411 |
| 6,139,183 A | * 10/2000 | Graumann | .................. 378/206 |
| 6,213,638 B1 | 4/2001 | Rattner | |

FOREIGN PATENT DOCUMENTS

DE 19950793 10/1999

* cited by examiner

Primary Examiner—Robert H. Kim
Assistant Examiner—Jurie Yun
(74) Attorney, Agent, or Firm—Schiff Hardin & Waite

(57) ABSTRACT

The invention is directed to a mobile X-ray apparatus having an X-ray system comprising an X-ray source and an X-ray detector that is arranged at a carrier device. For registering a series of 2D projections of a subject, the carrier device is pivotable under motor drive around an axis that proceeds at least essentially horizontally through the carrier device. The X-ray apparatus comprises means for generating a 3D image dataset from the registered 2D projections. The invention is also directed to a method for determining the projection geometries required for producing a 3D image dataset from registered 2D projections.

6 Claims, 1 Drawing Sheet

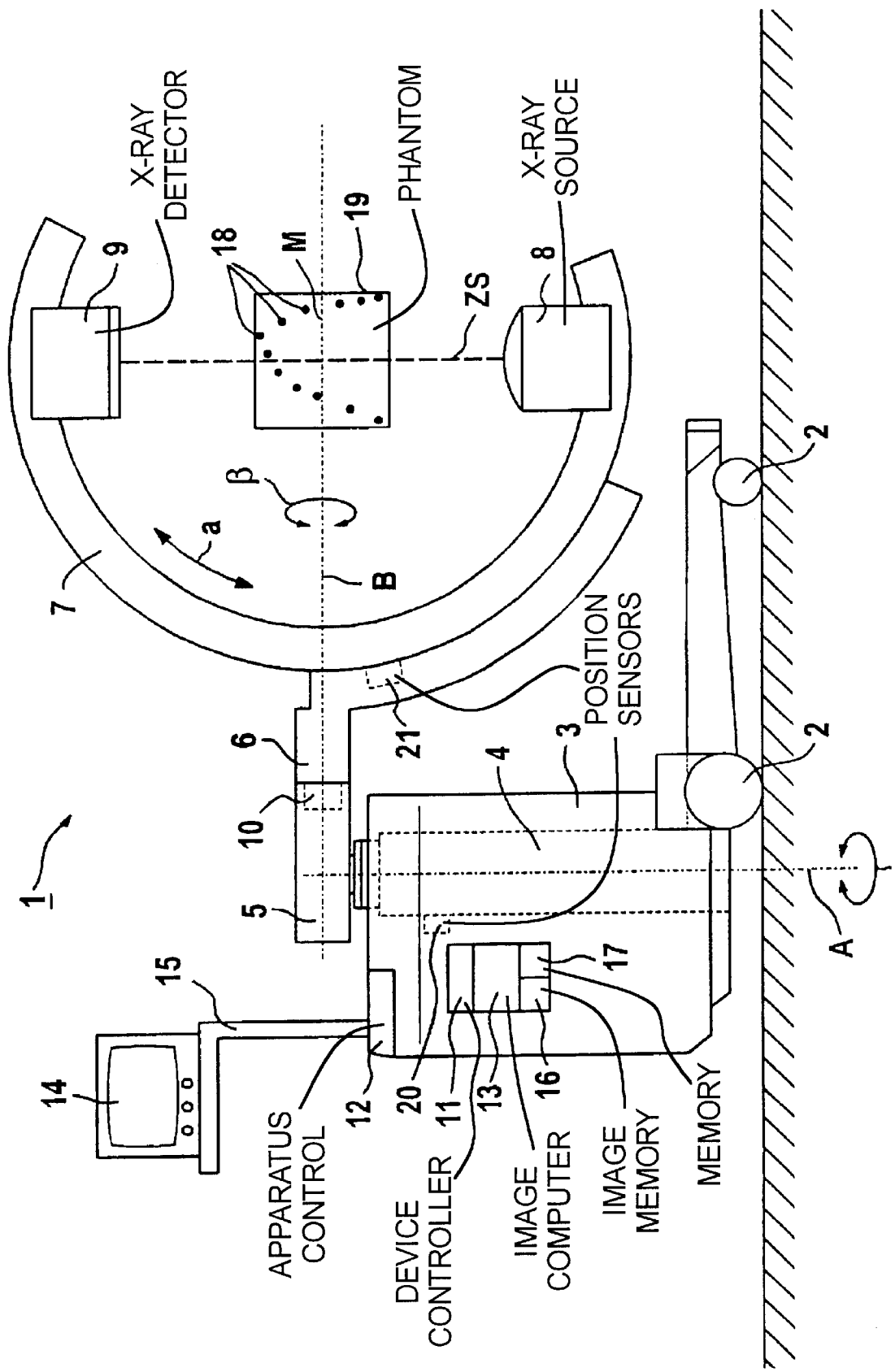

MOBILE X-RAY APPARATUS AND METHOD FOR DETERMINING PROJECTION GEOMETRIES THEREIN

BACKGROUND OF THE INVENTION

1. Field of the Invention

The present invention is directed to a mobile X-ray apparatus with an X-ray system having an X-ray source and an X-ray detector, of the type wherein the X-ray system is arranged at a carrier device so as to be adjustable relative to a subject for registering a series of 2D projections of the subject for the reconstruction of a 3D image of the subject. The invention is also directed to a method for determining projection geometries for such an X-ray apparatus.

2. Description of the Prior Art

X-ray apparatuses of the above type, which are usually a mobile C-arm X-ray apparatus, are used, for example, in medicine to reconstruct 3D images of a body part of a patient from a series of 2D projections of the body part registered from different projection angles. The reconstruction of 3D images from the 2D projections registered with the X-ray system, however, assumes a knowledge of the projection geometries, i.e. knowledge of the positions of the X-ray source and of the X-ray detector, as well as knowledge of the projection angle at each of the individual 2D projections. Since C-arm X-ray apparatuses exhibit mechanical instabilities, particularly relating to the adjustment motion of the C-arm, which are expressed in twisting of the C-arm given adjustment motions thereof due to the weight of the X-ray source and of the X-ray receiver, special measures must be provided in order to determine the projection geometries during the 2D projections, and thus to allow reconstruction of 3D images of the subject.

German OS 197 46 093 discloses a C-arm X-ray apparatus of this type. For registering a series of 2D projections, the C-arm of the X-ray apparatus provided with the X-ray system is preferably adjusted isocentrically along its circumference, known as an orbital motion, under motor drive in an angular range of approximately 200° around the body part of the patient to be examined. For determining the projection geometries, the X-ray apparatus has acoustic or electromagnetic transmitter devices arranged at the X-ray source and at the X-ray receiver, and receiver devices arranged at components of the X-ray apparatus that are stationary relative to the X-ray system. The projection geometries of the individual 2D projections are determined by transit time or phase measurements of the acoustic or electromagnetic waves between the transmitter and receiver devices during the course of registering 2D projections, and 3D images of the examined subject are thus generated from the series of 2D projections.

It has proven disadvantageous in the known X-ray apparatus that the realization of the motorized adjustment of the C-arm along its circumference is technically complicated and thus expensive. Moreover, the determination of the projection geometries during the registration of a series of 2D projections, which is also referred to as online determination of the projection geometries, requires a high use of computing power in order to obtain 3D images of the subject as desired in an optimally short time after the registration of the series of 2D projections. A real-time reconstruction of 3D images, accordingly, is only possible with utilization of an expensive computer exhibiting high computing performance.

SUMMARY OF THE INVENTION

An object of the present invention is to provide an X-ray apparatus of the type initially described wherein the technical outlay for producing 3D images of a subject is reduced. A further object of the invention is to provide a method with which the projection geometries required for the reconstruction of 3D images can be made available for the inventive X-ray apparatus in a simplified way.

According to the invention, the first object is achieved in a movable (mobile) X-ray apparatus having an X-ray system with an X-ray source and an X-ray detector that is arranged at a carrier, the carrier being pivotable under motor drive around an axis proceeding substantially horizontally through the carrier device for registering a series of 2D projections of a subject, and means for producing a 3D image dataset from the registered 2D projections. Differing from known X-ray apparatuses, the carrier device of the inventive X-ray apparatus is pivotable under motor drive around an axis proceeding substantially horizontally through the carrier. The form of pivot around the horizontally proceeding axis, which corresponds to the angulation axis of the C-arm in an embodiment of the carrier of the inventive X-ray apparatus, can be significantly more simply realized than the technically complex, motorized orbital rotation of the C-arm, which is understood by those skilled in the art as adjustment of the C-arm along its circumference. As a result of the inventive fashioning of the X-ray apparatus, accordingly, the technical outlay for producing a 3D image dataset of a subject from which 3D images of the subject can be acquired is significantly reduced.

Another advantage of the invention is that a simple C-arm X-ray apparatus having a non-isocentrically adjustable C-arm can be implemented without complications by a C-arm that is pivotable around its angulation axis under motor drive, so that 3D image datasets for the reconstruction of 3D images of a subject can be acquired with such simple X-ray apparatus. For a non-isocentrically C-arm the position of the intersection between the central ray of an X-ray beam emitted by the X-ray source and the angulation axis does not change appreciably given pivoting of the C-arm around the angulation axis, as is the case given an orbital rotation of an isocentrically adjustable C-arm around the isocenter of the C-arm. As a result, the generation of a 3D image dataset from a series of 2D projections is simplified in both cases.

In a preferred embodiment of the invention the motorized pivot of the carrier device is effected by a digitally controlled drive. The drive, which is preferably controlled by software and which includes a stepping motor according to one embodiment of the invention, enables a precise pivoting of the carrier device around the horizontally proceeding axis, and various pivoted positions of the carrier device can be repeatedly set with high precision. Individual pivot positions in the adjustment motion of the C-arm can be repeatedly approached with a precision of up to 500 $\mu°$ with the stepping motor.

The object directed to the method is achieved in a method for determining the projection geometries for a mobile X-ray apparatus, wherein the carrier device is pivotable, relative to a holder of the X-ray apparatus, around an axis proceeding substantially horizontally through the holder and the carrier device, the method including the following method steps:

a) setting first exposure parameters covering the initial position of the carrier device relative to the holder;
b) arranging a phantom provided for determining the projection geometries relative to the X-ray system so that it can be penetrated by an X-ray beam proceeding from the X-ray source to the X-ray detector;
c) registering a series of 2D projections of the phantom during the motorized pivot of the carrier device relative to the holder around the horizontally proceeding axis;

d) interpreting the registered 2D projections of the phantom for determining the projection geometries for each of the 2D projections;

e) storing the determined projection geometries for the first exposure parameters; and f) repeating steps a) through e) as needed for modified exposure parameters.

When the carrier device of the X-ray apparatus is fashioned as C-arm that is mounted so as to be adjustable along its circumference in a support connected to the holder, in one version of the method for determining the projection geometries that the determination of the projection geometries be undertaken dependent on the position of the carrier device relative to the support.

In the inventive method, differing from known X-ray apparatus operating methods, the projection geometries are determined and stored in one or more calibration events preceding the registration of series of 2D projections of the subject instead of during the registration of a series of 2D projections of the subject, in order to make the projection geometries available for later measurements of series of 2D projections of subjects for generating 3D image datasets. The inventive method thus is based on the recognition that the twisting of the carrier device which occurs during the adjustment of the carrier device around the horizontally proceeding axis of the X-ray apparatus, as a result of the weight of the X-ray source and of the X-ray detector, can be considered as a mechanical constant, this twisting leading to deviations from the ideal adjustment motion of the X-ray system around the subject. Since the carrier device always exhibits approximately the same twisting given swivel motions under the same initial conditions relating to the adjustment motion of the carrier device, i.e. given the same exposure parameters, which also include the initial position of the carrier device, the pivot velocity of the carrier device, the approach and braking curve of the carrier device as well as the pivot angle, this assumption has proven justified. The pivot motion of the carrier device in the X-ray system around the horizontally proceeding axis can, accordingly, be considered reproducible. The projections geometries of the inventive X-ray apparatus therefore can be determined in one or more calibration events before the actual subject measurements, which is also referred to as offline determination of the projection geometries.

DESCRIPTION OF THE DRAWINGS

The FIGURE is a side view, with internal components being schematically shown of a mobile X-ray apparatus constructed and operating in accordance with the invention.

DESCRIPTION OF THE PREFERRED EMBODIMENTS

The inventive X-ray apparatus shown in the FIGURE is a C-arm X-ray apparatus 1 having an apparatus carriage 3 mobile on wheels 2. The C-arm X-ray apparatus 1 has a lifting column 4 indicated with broken lines in the FIGURE which is rotatable around a longitudinal axis A in the directions of the double arrow a. A holder 5 is arranged at the lifting column 4, a support for a C-arm 7 being in turn arranged at the holder 5.

The C-arm 7 is provided with an X-ray system formed by an X-ray source 8 and a planar X-ray detector 9. The X-ray source 8 and the X-ray detector 9 are arranged opposite one another at the ends of the C-arm 7 such that a central ray ZS of a conical X-ray beam emanating from the X-ray source 8 strikes the X-ray detector 9 approximately centrally. The X-ray detector 9 can be an X-ray image intensifier, an aSi flat image detector or X-ray film. The C-arm 7, which is connected to the lifting column 4 via a support 6 and the holder 5, is vertically adjustable relative to the apparatus carriage 3 with the assistance of the lifting column 4.

In the exemplary embodiment, the C-arm 7 is seated at the support 6 so as to be adjustable, particularly manually adjustable along its circumference in the direction of the double arrow a. The support 6 together with the C-arm 7 is pivotable in a motor-driven manner around an axis B proceeding substantially horizontally through the holder 5, the support 6 and the C-arm 7, that is also referred to as angulation axis of the C-arm X-ray apparatus 1 (see double arrow β). For the motorized pivot of the support 6 and of the C-arm 7 relative to the holder 5, a digital software-controlled, electrical drive in the form of a stepping motor integrated into the holder 5 is provided in the exemplary embodiment. The digitally drivable stepping motor 10 allows individual pivot positions of the support 6 and of the C-arm 7 relative to the support 6 to be reproducibly approached with a precision of up to 500 $\mu°$. The control of the stepping motor 10 ensues with an device controller 11 of the C-arm X-ray apparatus 1 that, in the exemplary embodiment, also controls all other functions and components of the C-arm X-ray apparatus 1 related to the registration of 2D projections.

The device controller 11 is connected to an apparatus control console 12 of the C-arm X-ray apparatus 1 at which an operator can enter settings to the C-arm X-ray apparatus 1 that relate to the registration of 2D projections and the motorized adjustment of the support 6 together with the C-arm 7.

The C-arm X-ray apparatus 1 is provided for producing a 3D image dataset of a subject (not shown in the FIGURE). The 3D image dataset is generated with an image computer 13 connected to the device controller 11, from a series of 2D projections of the subject registered from projections angles differing from one another that are acquired with the X-ray system formed by the X-ray source 8 and the X-ray detector 9. The image computer 13 can reconstruct various 3D images or views of the radiologically examined subject from the generated 3D image dataset in a prescribable way. The 3D images or views can be displayed on a viewing device 14 that is arranged on a holder 15 of the C-arm X-ray apparatus 1.

For registering a series of 2D projections from different projection angles, the support 6 together with the C-arm 7 carrying the X-ray system is pivoted under motor drive around the examination subject under for which 3D image is to be obtained. This pivoting takes place in the direction of the double arrow β in an angular range of, preferably, greater than equal to 180° proceeding, for example, from the initial position of the C-arm 7 shown in the FIGURE. A series of approximately 50 through 100 2D projections of the subject are registered with the X-ray system during this motorized pivoting of the C-arm 7 around the angulation axis B. The registered 2D projections are intermediately stored in an image store 16. The inputs required for the registration of the series of 2D projections, for example the setting of the pivot velocity and of the pivot angle as well as the number of desired 2D projections, ensures via the control console 12.

For generating a 3D image dataset from the registered 2D projections, as already mentioned, knowledge of the projection geometries, i.e. the position of the X-ray source 8 and of the X-ray detector 9 relative to the subject, as well as knowledge of the projection angle at each of the 2D projections, is required.

In the inventive C-arm X-ray apparatus 1, these projection geometries are determined in a calibration event preceding the registration of the series of 2D projections of a subject, and are stored in a memory 17 for the later production of a respective 3D image dataset from the registered series of 2D projections respectively for different subjects.

Given pivoting of the C-arm 7 around the angulation axis B, twisting of the C-arm 7 occurs as a result of the weight of the X-ray source 8 and of the X-ray detector 9. Since this twisting, however, always occurs in approximately the same way under the same initial conditions, i.e. the same exposure parameters, for example the initial position of the C-arm 7 at the beginning of a pivot motion, the pivoting velocity, the approach and braking acceleration of the C-arm 7 and the pivot angle, this twisting can be viewed as a mechanical constant. Given known exposure parameters in the pivoting of the C-arm 7, accordingly, the adjustment path of the X-ray system, i.e. of the X-ray source 8 and of the X-ray receiver 9, can be reproduced. This adjustment path does not correspond to the ideal adjustment path due to the twisting of the C-arm 7. It has proven especially advantageous that individual pivot positions of the C-arm 7 can be reproducibly approached with high precision with the stepping motor 10. Considering the twists of the C-arm 7 as mechanical constants as well as the possibility of repeated, precise setting of individual pivot positions of the C-arm 7, accordingly, it is possible to determine the projection geometries for the C-arm X-ray apparatus 1 for different exposure parameters in one or more calibration events before the registration of series of 2D projections of a subject.

In the exemplary embodiment, this offline determination of the projection geometries ensues such that a first vertical adjustment of the support 6, a first adjustment of the C-arm 7 in the support 6 and a first adjustment of the support 6 relative to the holder 5 is first undertaken. For this purpose the device controller 11 interrogates the vertical adjustment of the holder 5 and the adjustment of the C-arm 7 relative to the support 6 from known position sensors 20, 21 schematically shown in the FIGURE, at the beginning of a calibration event. The position of the support 6 relative to the holder 5 can be directly derived from the control data for the stepping motor 10. In the exemplary embodiment, the C-arm 7 has been manually adjusted in the support 6 and fixed with known means (for example clamp screws, that are not shown in detail) so that the central ray ZS of an X-ray beam proceeding from the X-ray source 8 intersects the angulation axis B approximately at a right angle. A fixing of the C-arm 7 thus is not compulsory. Subsequently, a phantom 19 provided with X-ray-positive marks is arranged relative to the X-ray system for determining the projection geometries so that an X-ray beam proceeding from the X-ray source 8 to the X-ray detector 9 can at least partially penetrate the phantom 19. The phantom 19 can, for example, be a marker ring as disclosed in U.S. Pat. No. 5,822,396 or U.S. Pat. No. 5,835,563 that is actually provided for the online determination of projection geometries. Other phantoms specifically provided for the online determination of projection geometries also can be employed.

When, for example, the phantom 19 is a marker ring as disclosed in the aforementioned patents, and thus has a middle axis M, or if some other phantom having a middle axis M is used, the positioning of the phantom 19 relative to the X-ray system preferably ensues such that the middle axis M of the phantom is substantially parallel to, or coincident with, the angulation axis B of the C-arm X-ray apparatus 1.

After the positioning of the phantom 19 relative to the X-ray system, a series of 2D projections of the phantom 19 is prepared in a calibration mode, by moving the support 6 together with the C-arm 7 around the angulation axis B with the stepping motor 10, i.e. in a direction of the double arrow $\beta$, with a prescribable speed as well as a prescribable approach and braking acceleration. By interpreting the 2D projections of the phantom 19, for example with the image computer 13, the projection geometries for the individual 2D projections of the series are determined in a known way and are stored in the memory 17 dependent on the selected parameters in the registration of the 2D projections, i.e. dependent on the height setting of the holder 5, the initial position of the C-arm 7 relative to the holder 5, the initial position of the support 6 relative to the holder 5, the selected adjustment speed, as well as the selected adjustment angle. As warranted, further series of 2D projections can be prepared in the course of the calibration event for initial settings deviating from the initial positions of the C-arm 7 shown in the FIGURE, as well as for other exposure parameters. The projection geometries for the individual 2D projections are determined on the basis of the 2D projections and are stored in the memory 17 dependent on the exposure parameters.

In this way, appertaining datasets of projection geometries are obtained for various exposure parameters, these being employed in a later, corresponding selection of the exposure parameters for generating a 3D image dataset from a series of 2D projections registered for a subject. Given subject measurements, i.e. in the registration of 2D projections, approximately the same pivot positions of the C-arm 7 as were assumed by the C-arm 7 in the calibration are presumed, so that the corresponding projection geometries can be taken directly from the memory 17 and utilized for the generation of a 3D image dataset.

The inventive X-ray apparatus has been described above with reference to the example of a mobile C-arm X-ray apparatus 1. The inventive X-ray apparatus, however, need not necessarily be a C-arm X-ray apparatus but can be some other mobile X-ray apparatus that, for example, has a u-shaped carrier device.

Over and above this, the X-ray apparatus need not offer all adjustment possibilities for the X-ray system that were described for the C-arm X-ray apparatus 1. For example, the adjustability of the C-arm in circumferential direction or the height adjustment of the holder 5 can be foregone.

Some other type of drive can also be employed instead of the stepping motor insofar as this enables a repeated, precise setting of various pivot positions of the C-arm 7.

The electrical connections between electrically operated components of the C-arm X-ray apparatus 1 are not explicitly shown in the present exemplary embodiment since they are implemented in a known way.

The determination of the projection geometries for the inventive X-ray apparatus, moreover, need not necessarily ensue with the described offline calibration. On the contrary, the projection geometries can also be determined online, during subject measurements.

Although modifications and changes may be suggested by those skilled in the art, it is the intention of the inventors to embody within the patent warranted hereon all changes and modifications as reasonably and properly come within the scope of their contribution to the art.

We claim as our invention:

1. A mobile X-ray apparatus comprising:
   an X-ray system having a carrier with an X-ray source and an X-ray detector attached thereto;
   a holder for said carrier for rotatably mounting said carrier so that a substantially horizontal axis proceeds through said carrier;

a motor drive connected to said carrier for rotating said carrier around said substantially horizontal axis, while said X-ray apparatus is activated to emit X-rays, for registering a series of 2D projections of a subject disposed between said X-ray source and said X-ray detector; and a computer supplied with said 2D projections for generating a 3D image dataset from said 2D projections.

2. A mobile X-ray apparatus as claimed in claim 1 wherein said carrier is a C-arm.

3. A mobile X-ray apparatus as claimed in claim 1 wherein said motor is a digitally controlled motor.

4. A mobile X-ray apparatus as claimed in claim 3 wherein said digitally controlled motor is a stepping motor.

5. A method for determining projection geometries for a mobile X-ray apparatus having a carrier to which an X-ray source and an X-ray detector are attached, said carrier being rotatably being mounted to a holder with an axis proceeding substantially horizontally through said holder, said method comprising the steps of:

(a) setting first exposure parameters for an initial position of said carrier relative to said holder;

(b) disposing a phantom relative to said X-ray source and said X-ray detector so that said X-ray detector receives X-rays from said X-ray source attenuated by said phantom;

(c) rotating said X-ray source and said X-ray detector around said phantom by motor drive of said carrier, while emitting X-rays from said X-ray source, to register a series of 2D projections of said phantom;

(d) interpreting said 2D projections of said phantom for determining respective projection geometries for the 2D projections;

(e) storing said projection geometries for said first exposure parameters; and (f) if modified exposure parameters are set, repeating steps (a) through (e) for said modified exposure parameters.

6. A method as claimed in claim 5 comprising the steps of providing a C-arm as said carrier, and mounting said carrier at said holder for movement along a circumference of said C-arm.

\* \* \* \* \*